US 7,029,443 B2

(12) United States Patent
Kroll

(10) Patent No.: US 7,029,443 B2
(45) Date of Patent: Apr. 18, 2006

(54) SYSTEM AND METHOD FOR MONITORING BLOOD GLUCOSE LEVELS USING AN IMPLANTABLE MEDICAL DEVICE

(75) Inventor: Mark W. Kroll, Simi Valley, CA (US)

(73) Assignee: Pacesetter, Inc., Sylmar, CA (US)

(*) Notice: Subject to any disclaimer, the term of this patent is extended or adjusted under 35 U.S.C. 154(b) by 584 days.

(21) Appl. No.: 10/277,468

(22) Filed: Oct. 21, 2002

(65) Prior Publication Data

US 2004/0078065 A1 Apr. 22, 2004

(51) Int. Cl.
*A61B 5/145* (2006.01)
*A61B 5/0452* (2006.01)
*A61N 1/362* (2006.01)

(52) U.S. Cl. .................. 600/365; 600/513; 607/22
(58) Field of Classification Search .............. 607/5, 607/9, 22, 25, 18; 600/300, 347, 509, 513; 604/65–67
See application file for complete search history.

(56) References Cited

U.S. PATENT DOCUMENTS

| 4,731,051 | A | 3/1988 | Fischell ................. 604/67 |
| 4,947,845 | A | 8/1990 | Davis .................... 128/637 |
| 5,741,211 | A | 4/1998 | Renirie et al. ........... 600/300 |
| 5,919,216 | A | 7/1999 | Houben et al. ............ 607/72 |
| 6,272,379 | B1 | 8/2001 | Fischell et al. ........... 607/5 |
| 6,353,226 | B1* | 3/2002 | Khalil et al. ........... 250/341.8 |
| 6,572,542 | B1 | 6/2003 | Houben et al. ........... 600/300 |
| 2002/0026141 | A1 | 2/2002 | Houben et al. ........... 604/66 |
| 2003/0199925 | A1* | 10/2003 | Houben .................... 607/2 |

FOREIGN PATENT DOCUMENTS

| WO | WO 97/15227 | 5/1997 |
| WO | WO 03/088832 A1 | 10/2003 |

OTHER PUBLICATIONS

Krishen, A., et al. "Implantable Cardioverter Defibrillator T Wave Oversensing Caused by Hyperglycemia," PACE, vol. 24, No. 11, pp. 1701-1703, Nov. 2001.

* cited by examiner

*Primary Examiner*—Jeffrey R. Jastrzab
*Assistant Examiner*—John D Alexander

(57) ABSTRACT

T-wave amplitude and QT interval are derived from patient cardiac signals. Then blood glucose levels are determined based on a combination of the T-wave amplitude and the QT interval. By using a combination of both T-wave-based and QT interval-based signals, blood glucose levels can be reliably detected throughout a wide range of blood glucose levels. Once the blood glucose level has been detected, the implanted device compares the blood glucose level against upper and lower acceptable bounds and appropriate warning signals are generated if the level falls outside the bounds. In one example, wherein an implantable insulin pump is additionally provided, the pump is controlled based on the detected blood glucose level to maintain glucose levels within an acceptable range. A calibration technique is also provided for determining patient-specific parameters for use in the detection of blood glucose levels.

19 Claims, 8 Drawing Sheets

SYSTEM AND METHOD FOR MONITORING BLOOD GLUCOSE LEVELS USING AN IMPLANTABLE MEDICAL DEVICE

CROSS-REFERENCE TO RELATED APPLICATIONS

This application is related to copending U.S. patent application Ser. No. 10/277,467, filed Oct. 21, 2002, titled "System and Method for Monitoring Blood Glucose Levels Using an Implantable Medical Device."

FIELD OF THE INVENTION

The invention relates generally implantable medical devices, such as pacemakers or implantable cardioverter/defibrillators (ICDs), and in particular to implantable medical devices provided with the capability of monitoring blood glucose levels.

BACKGROUND OF THE INVENTION

Diabetic patients need to frequently monitor blood glucose levels to ensure that the levels remain within acceptable bounds and, for insulin dependent diabetics, to determine the amount of insulin that must be administered. Conventional techniques for monitoring blood glucose levels, however, leave much to be desired. One conventional technique, for example, requires that the patient draw blood, typically by pricking the finger. The drawn blood is then analyzed by a portable device to determine the blood glucose level. The technique can be painful and therefore can significantly discourage the patient from periodically checking blood glucose levels. Moreover, since an external device is required to analyze the blood, there is the risk that the patient will neglect to keep the device handy, preventing periodic blood glucose level monitoring. For insulin-dependent diabetics, failure to properly monitor blood glucose levels can result in improper dosages of insulin causing, in extreme cases, severe adverse health consequences such as a ketoacidotic diabetic coma, which can be fatal. Accordingly, there is a significant need to provide a reliable blood glucose monitoring technique, which does not rely on the patient to monitoring his or her own glucose levels and which does not require an external analysis device.

In view of the many disadvantages of conventional external blood glucose monitoring techniques, implantable blood glucose monitors have been developed, which included sensors for mounting directly within the blood stream. However, such monitors have not achieved much success as the glucose sensors tend to clog over very quickly. Thus, an implantable device that would continually and reliably measure blood glucose levels without requiring glucose sensors would be very desirable. Moreover, as with any implantable device, there are attended risks associated with implanting the blood glucose monitor, such as adverse reactions to anesthetics employed during the implantation procedure or the onset of subsequent infections. Hence, it would be desirable to provide for automatic blood glucose level monitoring using medical devices that would otherwise need to be implanted anyway, to thereby minimize the risks associated with the implantation of additional devices. In particular, for patients already requiring implantation of a cardiac stimulation device, such as a pacemaker or ICD, it would be desirable to exploit features of electrical cardiac signals routinely detected by the implantable device for use as a proxy to estimate blood glucose levels.

Two potential proxies for the electrocardiographic monitoring for blood glucose levels have been investigated but are not attractive by themselves. One potential proxy for blood glucose levels is the corrected QT interval (QTc); another is T-wave amplitude. Both vary to a certain extent as a function of the blood glucose levels. More specifically, QTc interval tends to decrease with increasing blood glucose levels, at least up to a certain blood glucose level (beyond which the QTc interval does not change.) T-wave amplitudes tend to increase with increasing blood glucose levels, at least for relatively low blood glucose levels. At higher glucose levels, however, T-wave amplitude tends to decrease with increasing blood glucose level. Hence, QTc interval appears to be effective as a proxy for blood glucose levels only at low levels. Meanwhile, T-wave amplitude behavior is bimodal as it can be lowered by low glucose levels as well as by high glucose levels and hence appears to be ambiguous and ineffective as a proxy.

Thus, heretofore, QTc interval and T-wave amplitude have not been effectively exploited in the monitoring of blood glucose levels. However, as QTc interval and T-wave amplitude each appear to be affected by blood glucose levels, it would be desirable to provide an improved technique which, despite the individual deficiencies of QTc intervals and T-wave amplitudes, nevertheless achieves reliable detection of the blood glucose levels, and it is to this end that aspects of the invention are drawn. In particular, aspects of the invention are directed to providing an implantable cardiac stimulation device with the capability of monitoring blood glucose levels based upon electrocardiographic signals. Other aspects of invention are directed to providing a system and method for programming and calibrating the implanted device for use with individual patients to ensure reliable and accurate operation of the device.

Insofar as exploiting features of electrocardiographic signals for the purposes of blood glucose level monitoring, at least one patent (U.S. Pat. No. 5,741,211 to Renirie) has alluded to the use of electrocardiographic signal features as a basis for detecting blood glucose levels, particularly QRS and T-waves. Renirie is primarily directed to a Holter-type external monitor, but has some discussion of implantable devices as well. Renirie mentions the possibility of using other features besides QRS and T-waves such as QT intervals and RR intervals but does not specifically indicate the desirability of combining QT intervals and T-waves. Moreover, the techniques of Renirie do not appear to be enabling as to the use of T-waves insofar as implantable device monitoring is concerned. For example, Renirie describes the use of a standard pacemaker lead for the purposes of measuring T-wave amplitudes. However, the conventional pacemaker lead simply does not appear capable of detecting T-wave amplitudes with the requisite degree of accuracy. In addition, Renirie fails to even mention the bimodal response of the T-wave amplitude referred to above or to provide any technique for addressing the ambiguities resulting from using T-wave amplitudes as a proxy for blood glucose levels. Moreover, insofar as QT intervals are concerned, Renirie makes no mention of employing corrected QT intervals. Accordingly, despite the speculative teachings of Renirie, significant technical challenges remain in implementing a working system that can optimally and reliably detect blood glucose levels based upon T-waves and QT intervals. Accordingly, still other aspects of the invention are directed toward overcoming the many technical challenges needed to provide a working system for detecting blood glucose levels via T-waves and QT intervals within an implantable medical device.

SUMMARY

In accordance with a first embodiment, a technique is provided for detecting blood glucose levels using an implantable medical device implanted within a patient. T-wave amplitude and QT interval are detected within patient cardiac signals. Blood glucose levels are derived based on a combination of both T-wave amplitude and QT interval. By exploiting a combination of both T-wave and QT interval-based signals, blood glucose levels can be reliably and unambiguously detected throughout a wide range of blood glucose levels despite the general lack of QT response at high blood glucose levels and despite the overall bimodal glucose response of T-wave amplitudes. Preferably, T-wave amplitudes are first converted to T-wave amplitude fractions and QT intervals are first converted to QTc before glucose levels are derived to provide for optimal blood glucose level monitoring.

In an exemplary embodiment, the implantable medical device is a pacemaker or ICD. Hence, blood glucose monitoring is conveniently provided within patients already requiring a pacemaker or ICD, without requiring implantation of additional devices. Moreover, by using an implantable device to detect blood glucose levels, no external blood-monitoring device is required and no painful finger prick techniques are needed. Hence, there is no risk the patient will fail to periodically detect blood glucose levels. Furthermore, blood glucose levels can be detected as often as needed, for example, once every five minutes. Once the blood glucose level has been detected, the implanted device compares the blood glucose level against acceptable upper and lower bounds and appropriate warning signals are generated if the level exceeds the acceptable bounds. If an implantable insulin pump is additionally provided, the insulin pump may be automatically controlled based on the detected blood glucose level to maintain the level within a pre-determined acceptable range.

In the exemplary embodiment, T-waves are detected using either a defibrillation coil, an enlarged ventricular lead or a series of smaller leads combined to provided a single strong ventricular signal providing the requisite degree of accuracy in the detection of T-waves. In any case, T-wave amplitude fraction is derived by inputting a T-wave baseline value, detecting cardiac electrical signals, measuring T-wave amplitude within the cardiac signals, and then converting T-wave amplitude into the T-wave amplitude fraction by subtracting the T-wave baseline value. QTc interval is detected by inputting a QT interval baseline value, measuring heart rate based on the cardiac electrical signals, measuring QT interval within the cardiac signals, then converting QT interval into a QTc interval based on the heart rate. The QTc interval is then converted into a QT interval delta by subtracting the QT baseline value and the blood glucose level is then determined based on a combination of the T-wave amplitude fraction and the QTc delta value. In one specific example, Blood Glucose Level=A−B*(QTc delta)−C*(T-wave amplitude fraction) wherein A, B and C are predetermined parameters or coefficients calibrated to the particular patient.

In accordance with a second aspect of the invention, a calibration technique is provided for determining patient-specific parameters for use in the detection of blood glucose levels by a blood glucose monitoring system within an implanted medical device. The technique is implemented using an external programmer device in communication with the implanted device. Initially, signals are received from the implanted device representative of internal patient electrical cardiac signals. Simultaneously, signals representative of the corresponding patient blood glucose levels of the patient are input. Based on the signals received from the implanted device and on the input blood glucose levels, patient-specific parameters are derived that relate patient electrical cardiac signals to blood glucose levels for the particular patient in which the medical device is implanted. The parameters are transmitted to the implanted device such that the implanted device can thereafter derive blood glucose levels from newly-detected patient electrical cardiac signals. In this manner, the blood glucose monitoring system of the implanted device is calibrated for the particular patient in which the device is implanted.

In an exemplary embodiment, blood glucose levels are input from an external blood glucose monitor mounted to the patient, which detects blood glucose levels using otherwise conventional techniques. The external blood glucose monitor is only employed during the calibration technique. The patient electrical cardiac signals are T-wave amplitude fractions and QTc delta values. In the example wherein Blood Glucose Level=A−B*(QTc delta)−C*(T-wave amplitude fraction), the coefficients A, B and C represent the patient-specific parameters determined by the calibration technique, which are then transmitted to the implanted device. To ensure that the parameters adequately represent a wide range of blood glucose levels, the parameters are calculated based on QT interval and T-wave data accumulated while the blood glucose level of the patient is caused to transition through a wide range of levels. More specifically, for non-insulin dependent patients, glucose is administered until the blood glucose level rises to an upper threshold, such as 300 mg/dl, then insulin is administered until the glucose level falls to a lower threshold, such as 40 mg/dl. For insulin-dependent patients, rather than administering glucose, it is sufficient to simply withhold insulin until the blood glucose level has naturally risen to the upper threshold, then to administer insulin to reduce the glucose levels to the lower threshold. In either case, QT interval and T-wave data is collected throughout the entire process to permit parameters to be generated that are properly representative of the entire range of glucose levels from the lower threshold to the upper threshold.

Thus, various techniques are provided for monitoring blood glucose levels based on proxies derived from electrocardiographic signals using an implanted medical device and for calibrating the device for use with individual patients. Other objects, features and advantages of the invention will be apparent from the detailed description to follow.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Stimulation Device

Figure 1:
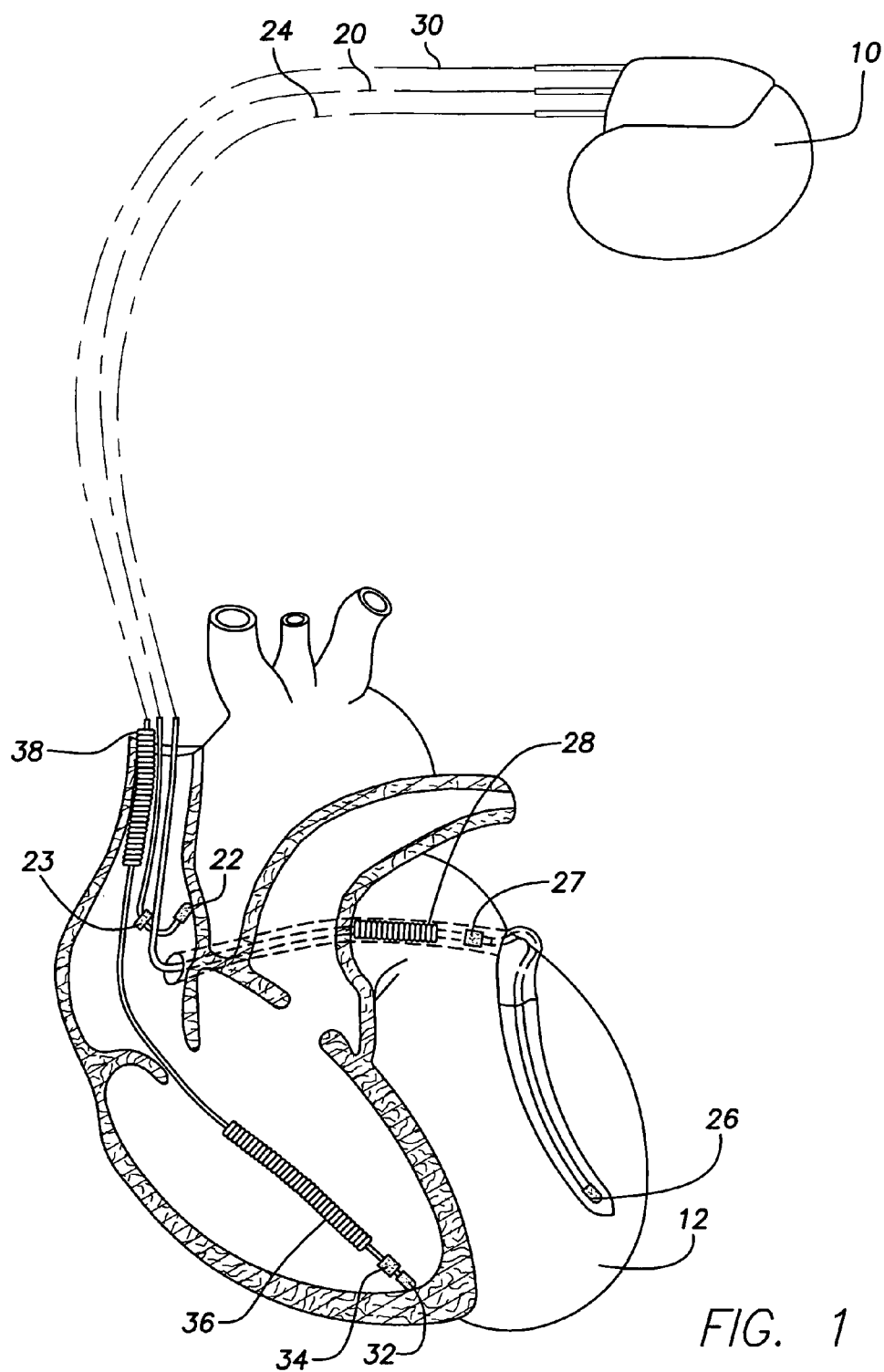
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

As will be explained below, accurate detection of QTc intervals and T-wave amplitudes within ventricular signals is necessary for the determination of blood glucose levels in accordance with the invention. For accurate measurements of the T-wave amplitude, one wants large-scale electrodes. RV coil electrode 36, configured for defibrillation, is sufficiently large to reliably measure QTc intervals and the T-wave amplitudes by detecting the voltage between the RV coil and the can.

Alternatively, rather than employing an RV coil configured for defibrillation, a set of smaller RV electrodes can instead be implanted with signals generated therefrom averaged together to yield a single ventricular signal having sufficient accuracy to reliably detect QTc intervals and the T-wave amplitudes. Again, voltage signals are detected between the individual electrodes and the can. Hence, the invention is not limited for use only with implanted devices having defibrillator coils but can be implemented within otherwise conventional pacemakers. Further information regarding the accurate detection of QT intervals is provided within "Measurement of High Resolution ECG QT Interval during Controlled Euglycaemia and Hypoglycaemia", Ireland, et al, (Physiol. Meas. Vol. 21, May 2000, pp 295–303), which is incorporated by reference herein.

Figure 2:
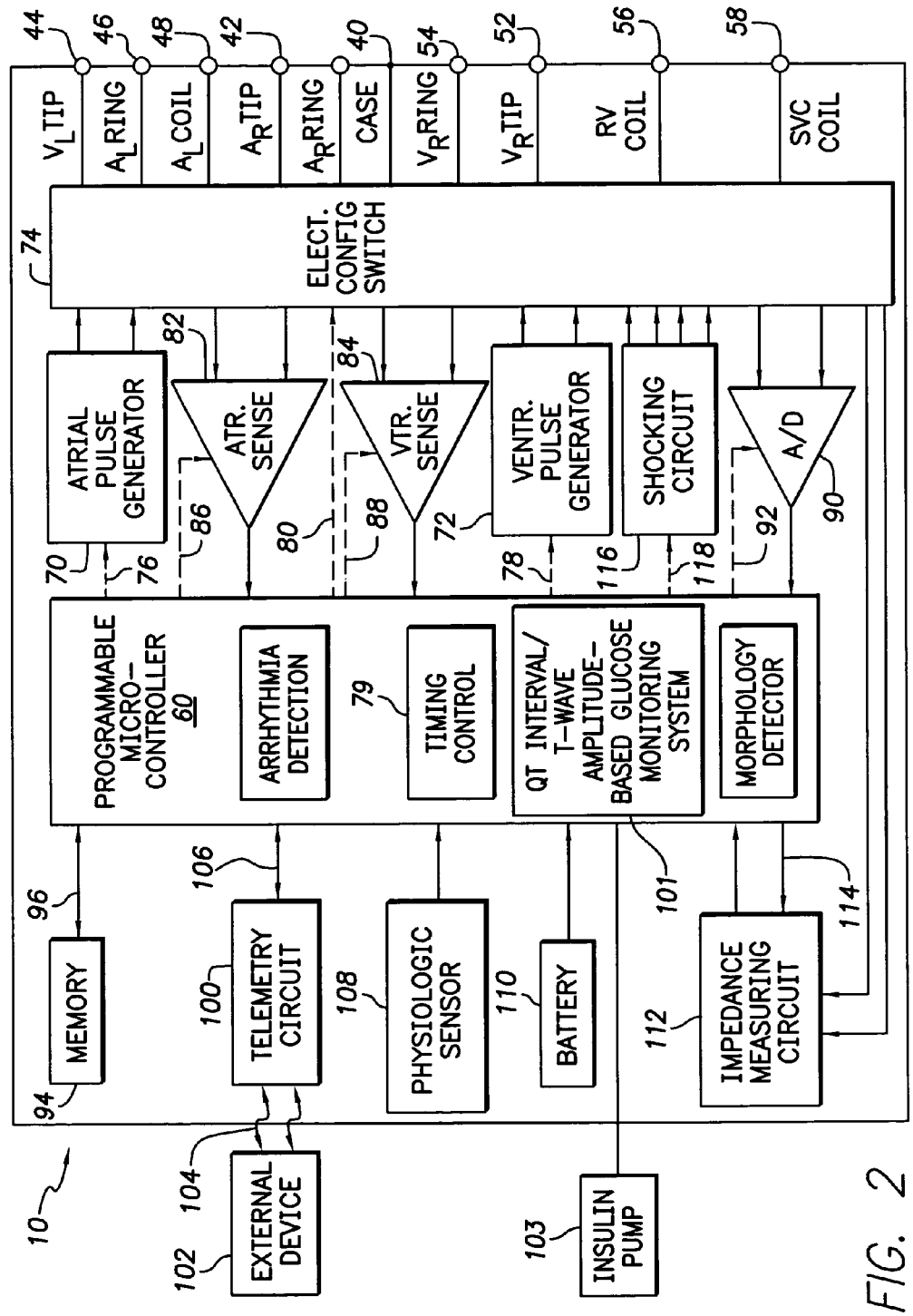
FIG. 2 is a functional block diagram of the multi-chamber implantable stimulation device of FIG. 2, illustrating the basic elements that provide cardioversion, defibrillation and/or pacing stimulation in four chambers of the heart and particularly illustrating a blood glucose monitoring system for automatically detecting glucose levels using both QTc intervals and T-wave amplitude fractions.

FIG. 2 illustrates a simplified block diagram of the multi-chamber implantable stimulation device 10 which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and/or pacing stimulation.

The stimulation device 10 includes a housing 40 which is often referred to as a "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the right atrial ($A_R$) tip electrode 22.

To achieve left chamber sensing, pacing and/or shocking, the connector includes at least a left ventricular ($V_L$) tip terminal 44, a left atrial ($A_L$) ring terminal 46, and a left atrial ($A_L$) shocking terminal (coil) 48, which are adapted for connection to the left ventricular tip electrode 26, the left atrial ring electrode 27, and the left atrial coil electrode 28, respectively.

To support right chamber sensing, pacing and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry or processor, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, ventricular interconduction (V—V) delay, pacing mode, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. If multiple RV electrodes are employed to generate a single averaged ventricular signal, then switch 74 is configured to allow the paralleling (or averaging) of the multiple RV electrodes to simulate a large electrode for accurate sensing of the T-wave.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

Each of the sensing circuits, 82 and 84, preferably employ one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window and, based on the amplitude of the sampled cardiac signal, determines if capture has occurred.

The microcontroller 60 is further coupled to a memory 94 by a suitable data/address bus 96, where the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the patient's heart 12 within each respective tier of therapy. A feature of the stimulation device 10 is the ability to sense and store a relatively large amount of data (e.g., from the data acquisition system 90), which data may then be used for subsequent analysis to guide the programming of the stimulation device 10.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through an established communication link 104.

A blood glucose monitoring unit 101 of the microcontroller processes signals representative of QT intervals and T-wave amplitude fractions and, using parameters previously generated by external device 102, derives the current blood glucose level within the bloodstream of the patient. If an insulin pump 103 is provided, the blood glucose monitoring unit transmits control signals to the insulin pump for adjusting the amount of insulin delivered to the patient in view of the current blood glucose levels. Information regarding implantable insulin pumps may be found in U.S. Pat. No. 4,731,051 to Fischell and in U.S. Pat. No. 4,947,845 to Davis, both of which are incorporated by reference herein. The insulin pumps discussed therein, or other suitable insulin pumps, are modified as needed to permit receipt of control signals from glucose monitoring unit 101. The operation of the blood glucose monitoring unit is described in detail below with reference to FIG. 4.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time and also be capable of providing high-current pulses (for capacitor charging) when the patient requires a shock pulse. The battery 110 must preferably have a predictable discharge characteristic so that elective replacement time can be detected. Accordingly, the stimulation device 10 can employ lithium/silver vanadium oxide batteries.

The stimulation device 10 further includes a magnet detection circuitry (not shown), coupled to the microcontroller 60. The purpose of the magnet detection circuitry is to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 via a control signal 114. Certain applications for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 112 is advantageously coupled to the switch bank 74 so that any desired electrode may be used.

It is a primary function of the stimulation device 10 to operate as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high (11–40 joules) energy, as controlled by the microcontroller 60. Such shocking pulses are applied to the patient's heart through at least two shocking electrodes, as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (e.g., using the RV electrode as a common electrode).

Cardioversion shocks are generally considered to be of low to moderate energy level (so as to minimize pain felt by the patient), and/or synchronized with an R-wave, and/or pertaining to the treatment of tachycardia. Defibrillation shocks are generally of moderate to high energy level (i.e., corresponding to thresholds in the range of 5–40 joules), delivered asynchronously (since R-waves may be too disorganized) and pertaining exclusively to the treatment of fibrillation. Accordingly, the microcontroller 60 is capable of controlling the synchronous or asynchronous delivery of the shocking pulses.

Device Programmer Overview

Figure 3:
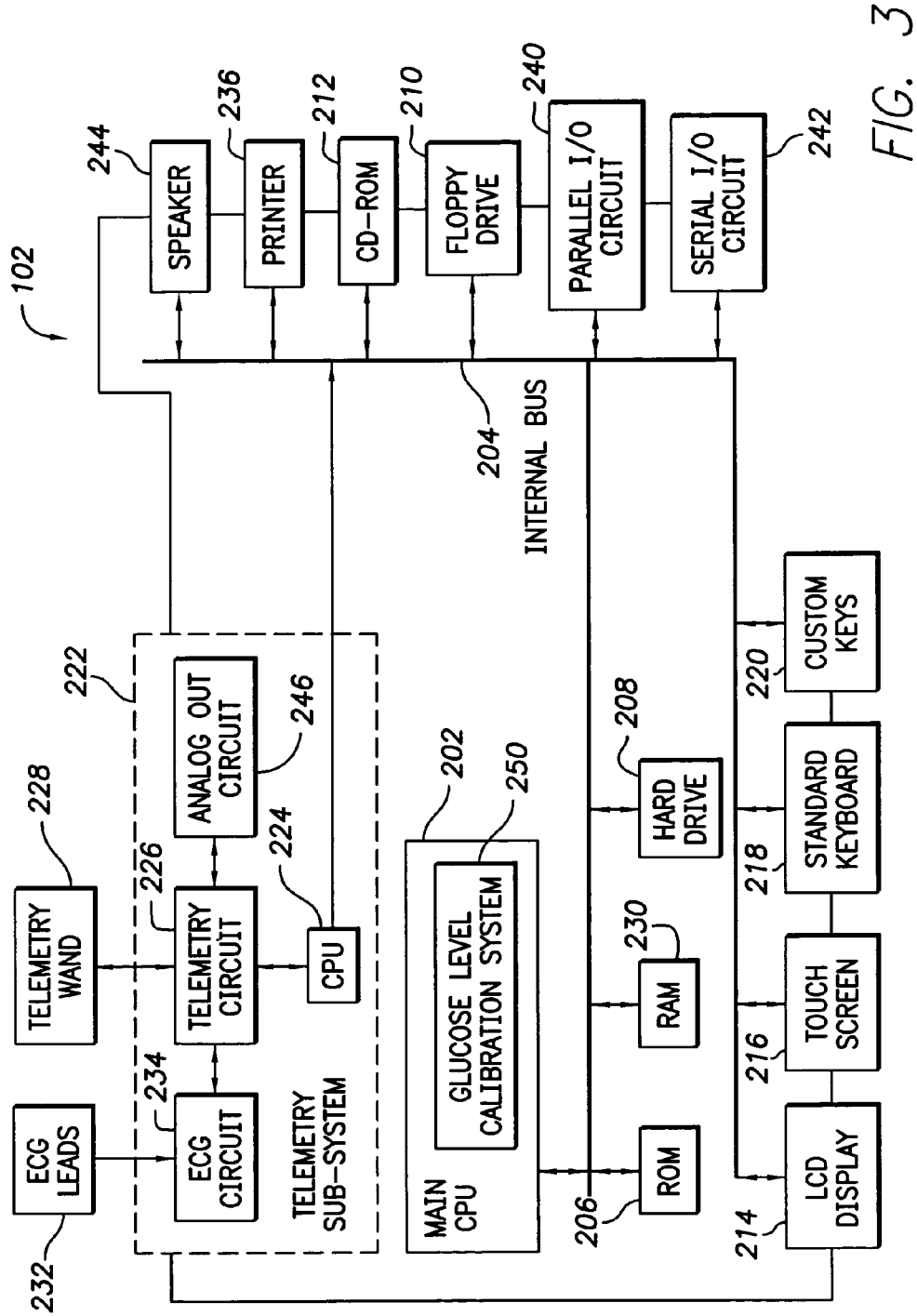
FIG. 3 is a functional block diagram illustrating components of a programmer for use in programming the implantable device of FIGS. 1 and 2, and in particular illustrating a calibration system for use in calibrating the blood glucose monitoring system of the implantable device.

FIG. 3 illustrates pertinent components of external programmer device 102 for use in programming an implantable medical device such as a pacemaker or ICD. Briefly, the programmer permits a physician or other user to program the operation of the implanted device and to retrieve and display information received from the implanted device such as IEGM data and device diagnostic data. Additionally, the external programmer receives and displays ECG data from separate external ECG leads that may be attached to the patient. Depending upon the specific programming of the external programmer, programmer 102 may also be capable of processing and analyzing data received from the implanted device and from the ECG leads to, for example, render preliminary diagnosis as to medical conditions of the patient or to the operations of the implanted device.

Now, considering the components of programmer 102, operations of the programmer are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206 and random access memory 230. Additional software may be accessed from a hard drive 208, floppy drive 210, and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Typically, the physician initially controls the programmer 102 to retrieve data stored within the implanted medical device and to also retrieve ECG data from ECG leads, if any, coupled to the patient. To this end, CPU 202 transmits appropriate signals to a telemetry subsystem 222, which provides components for directly interfacing with the implanted device, and the ECG leads. Telemetry subsystem 222 includes its own separate CPU 224 for coordinating the operations of the telemetry subsystem. Main CPU 202 of programmer communicates with telemetry subsystem CPU 224 via internal bus 204. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient near the implanted device to permit reliable transmission of data between the telemetry wand and the implanted device. Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted device is stored by external programmer 102 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 102, the implanted device may be further controlled to transmit additional data in real time as it is detected by the implanted device, such as additional IEGM data, lead impedance data, and the like. Additionally, or in the alternative, telemetry subsystem 222 receives ECG signals from ECG leads 232 via an ECG processing circuit 234. As with data retrieved from the implanted device itself, signals received from the ECG leads are stored within one or more of the storage devices of the external programmer. Typically, ECG leads output analog electrical signals representative of the ECG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time.

Thus, the programmer receives data both from the implanted device and from the external ECG leads. Data retrieved from the implanted device includes parameters representative of the current programming state of the implanted device. Under the control of the physician, the external programmer displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device. Prior to reprogramming specific parameters, the physician may control the external programmer to display any or all of the data retrieved from the implanted device or from the ECG leads, including displays of ECGs, IEGMs, and statistical patient information. Any or all of the information displayed by programmer may also be printed using a printer 236.

CPU 202 includes a glucose level calibration system 250 for generating patient-specific information for transmission to the glucose level monitoring system of the implanted device of FIG. 2, which the glucose level monitoring system then uses to facilitate glucose level determination. The operation of calibration system 250 is described in detail below primarily with reference to FIG. 5.

Programmer 102 also includes a modem (not shown) to permit direct transmission of data to other programmers via the public switched telephone network (PSTN) or other interconnection line, such as a T1 line or fiber optic cable. Depending upon the implementation, the modem may be connected directly to internal bus 204 may be connected to the internal bus via either a parallel port 240 or a serial port 242. Other peripheral devices may be connected to the external programmer via parallel port 240 or a serial port 242 as well. Although one of each is shown, a plurality of input output (IO) ports might be provided.

A speaker 244 is included for providing audible tones to the user, such as a warning beep in the event improper input is provided by the physician. Telemetry subsystem 222 additionally includes an analog output circuit 246 for controlling the transmission of analog output signals, such as IEGM signals output to an ECG machine or chart recorder.

With the programmer configured as shown, a physician or other user operating the external programmer is capable of retrieving, processing and displaying a wide range of information received from the ECG leads or from the implanted device and to reprogram the implanted device if needed. The descriptions provided herein with respect to FIG. 3 are intended merely to provide an overview of the operation of programmer and are not intended to describe in detail every feature of the hardware and software of the device and are not intended to provide an exhaustive list of the functions performed by the device.

In the remaining figures, flow charts are provided for illustrating the operation and novel features of various exemplary embodiments of the invention. In the flow chart, various algorithmic steps are summarized in individual "blocks". Such blocks describe specific actions or decisions to be made or carried out as the algorithm proceeds. Where a microcontroller (or equivalent) is employed, the flow charts presented herein provide the basis for a "control program" that may be used by such a microcontroller (or equivalent) to effectuate the desired control of the device. Those skilled in the art may readily write such a control program based on the flow charts and other descriptions presented herein.

Determination of Blood Glucose Levels

Figure 4:
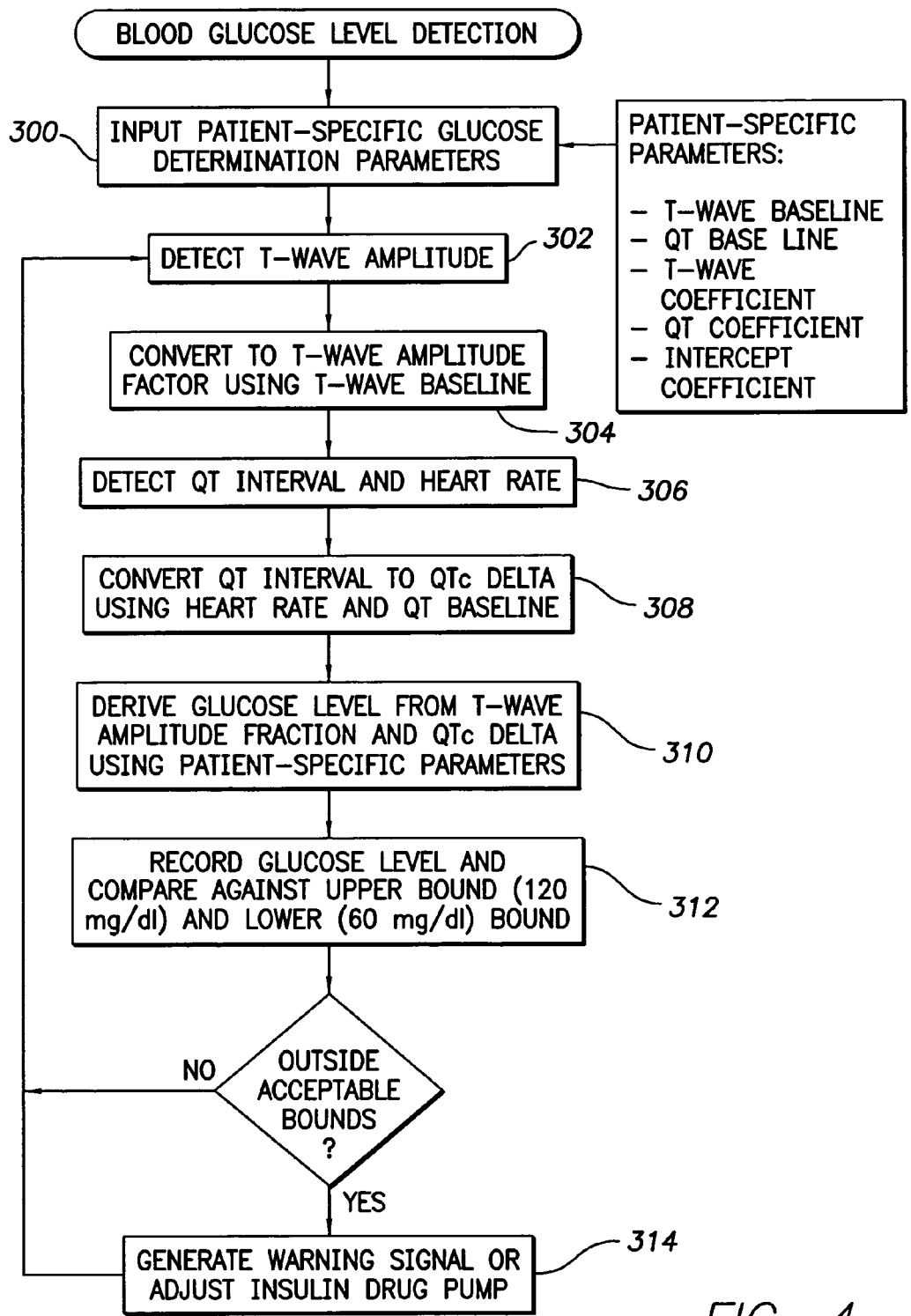
FIG. 4 is a flow diagram illustrating a method performed by the blood glucose monitoring system of FIG. 2 to detect glucose levels.

Referring now to FIG. 4, the operation of blood glucose monitoring system of 101 of FIG. 2 will be described. Initially, at steps 300 and 301, the monitoring system inputs a set of patient-specific parameters relating patient T-wave amplitude fractions and QT interval delta values to blood glucose levels. This data is preferably generated in advance using the technique of FIG. 5, then transmitted to the implanted device for storage therein. In one example, the blood glucose level is determined according to the following equation:

$$\text{Blood Glucose Level} = A - B^*(QTc\ \text{delta}) - C^*(T\text{-wave amplitude fraction}) \quad \text{Eq. 1}$$

wherein A, B and C represent some of the patient-specific parameters. More specifically, "A" represents a predetermined intercept coefficient, "B" represents a predetermined T-wave coefficient and "C" represents a predetermined QT coefficient. Typically, A is in the range of 250–270; B is in the range of 1.25–1.50; and C is in the range of 160–180. In a specific case, A=263.5, B=−1.35 and C=−171. Additionally, a T-wave baseline value and a QTc baseline value are input at step 300. The T-wave baseline value represents the average (or instead the median) T-wave amplitude for the patient and the QTc baseline represents the average QTc interval for the patient. In other examples wherein different equations or different techniques are employed for relating blood glucose levels to QT intervals and T-wave fractions, alternative patient-specific parameters are input of step 300. In any case, beginning at step 302, the implanted device detects T-wave amplitude with electrical signals received from the ventricular leads implanted within the heart of the patient. As mentioned in the discussion in FIG. 2, T-waves are preferably detected based on a voltage measurement between the can housing and a large ventricular defibrillation coil electrode or a combination of smaller electrodes averaged to simulate a large electrode. In addition, preferably, T-wave amplitude is derived based upon an average (or instead median) of some predetermined number of individually detected T-waves (such as the last 10 or 20 T-waves) or based on all T-waves detected in some fixed period of time (such as within the last 10 or 20 seconds). By using an average T-wave value, a single aberrant T-wave will not significantly affect the blood glucose calculation. In any case, at step 304, the monitoring unit converts the T-wave amplitude into a T-wave amplitude fraction by dividing the detected T-wave amplitude by the input T-wave baseline value.

At step 306, the implanted device detects QT interval and heart rate and, at step 308, converts the QT interval to a QTc delta value using the heart rate and the QT baseline values. More specifically, for each QT interval, the corresponding heart rate detected at the time the QT interval was detected is used to adjust the QT interval to yield a QTc interval. Then, the QTc interval is divided by the input QT baseline value to yield a QT delta value. As with T-waves, preferably a set of QTc interval delta values are averaged to ensure that a single individual aberrant QT interval will not unduly affect the determination of the blood glucose level. Alternatively, a median QTc may be used.

At step 310, the monitoring unit then estimates the current blood glucose level within the blood stream of the patient based on the T-wave amplitude fraction and the QTc delta. In the example wherein Eq. 1 is used, the equation is calculated using the derived values for T-wave amplitude fraction and QTc delta and the input patient-specific coefficients A, B and C. The calculated blood glucose level is then recorded within memory, at step 312, and compared against both an upper threshold and a lower threshold to ensure that the blood glucose level is within acceptable bounds. In one example, the upper threshold is 120 mg/dl and the lower threshold is 60 mg/dl. The upper and lower threshold values are preprogrammed within the system and may be specified, for example, by a physician using the external programmer. If the blood glucose level is found to be outside the acceptable bounds, a warning signal is generated at step 314 to alert the patient. Steps 302–314 are repeated continuously into loop to periodically update the blood glucose level measurement. For example, the measurement may be repeated once every minute, once every 15 minutes, or once every hour. Preferably, the frequency by which the blood glucose level is updated is programmed in advance by a physician using the external programmer.

Preferably, a different warning signal is provided at step 314 when the blood glucose level is too low than when it is too high. Depending upon the configuration of the implanted device, the warning signal may be generated by causing the pacemaker to periodically vibrate inside the patient. Alternatively, the pacemaker may transmit an electronic warning signal to an external warning device such as a bedside monitor or a pager-type device carried with the patient, which displays the warning for the patient. If a warning signal is transmitted to an external warning device, the exact blood glucose level is preferably also transmitted such that it can be displayed to the patient. In the alternative, if an external warning device is provided, the current blood glucose level may be transmitted periodically such that the patient is kept apprised of the current blood glucose level. In other words, this information is not transmitted only when the blood glucose level falls outside acceptable bounds but is transmitted periodically. In addition, since the blood glucose level is recorded in memory at step 312, this information may be subsequently transmitted to the external programmer device for review by a physician during a subsequent office visit. Note that a wide range of other diagnostic information is routinely detected and recorded by the implanted device, such as heart rate and the like. Accordingly, the blood glucose level the patient can be correlated with other diagnostic information to help the physician developed optimal therapies for the patient.

At step 314, if an insulin drug pump has been implanted within the patient, the monitoring unit transmits appropriate control signals to the drug pump for adjusting the amount of insulin provided to the patient based upon the blood glucose level. For example, if the blood glucose level has exceeded the upper bound, the drug pump is controlled to provide a greater amount of insulin to the patient. As with the generation of warning signals, control of the insulin drug pump is not limited only to circumstances in which the blood glucose level has exceeded the acceptable bounds. Rather, each newly calculated value for blood glucose level may be used to control the insulin pump to maintain the blood glucose level at a target level deemed by the physician to be optimal such as, for example, at 100 mg/dl. In one example, the insulin pump is additionally controlled to modulate the blood glucose level based upon the current activity level of the patient, for example, to increase the blood glucose level whenever the patient is more active and to decrease it otherwise. Additionally, other programmable features of the implanted device itself may be adjusted based upon blood glucose levels. As one example, if blood glucose levels are found to be particularly low, a base pacing rate may be reduced until the blood glucose levels return to acceptable levels. A wide variety of techniques may be employed for controlling an insulin pump or for controlling various functions of the implanted device itself and no attempt is made herein to describe all possible techniques.

Calibration Technique

Figure 5:
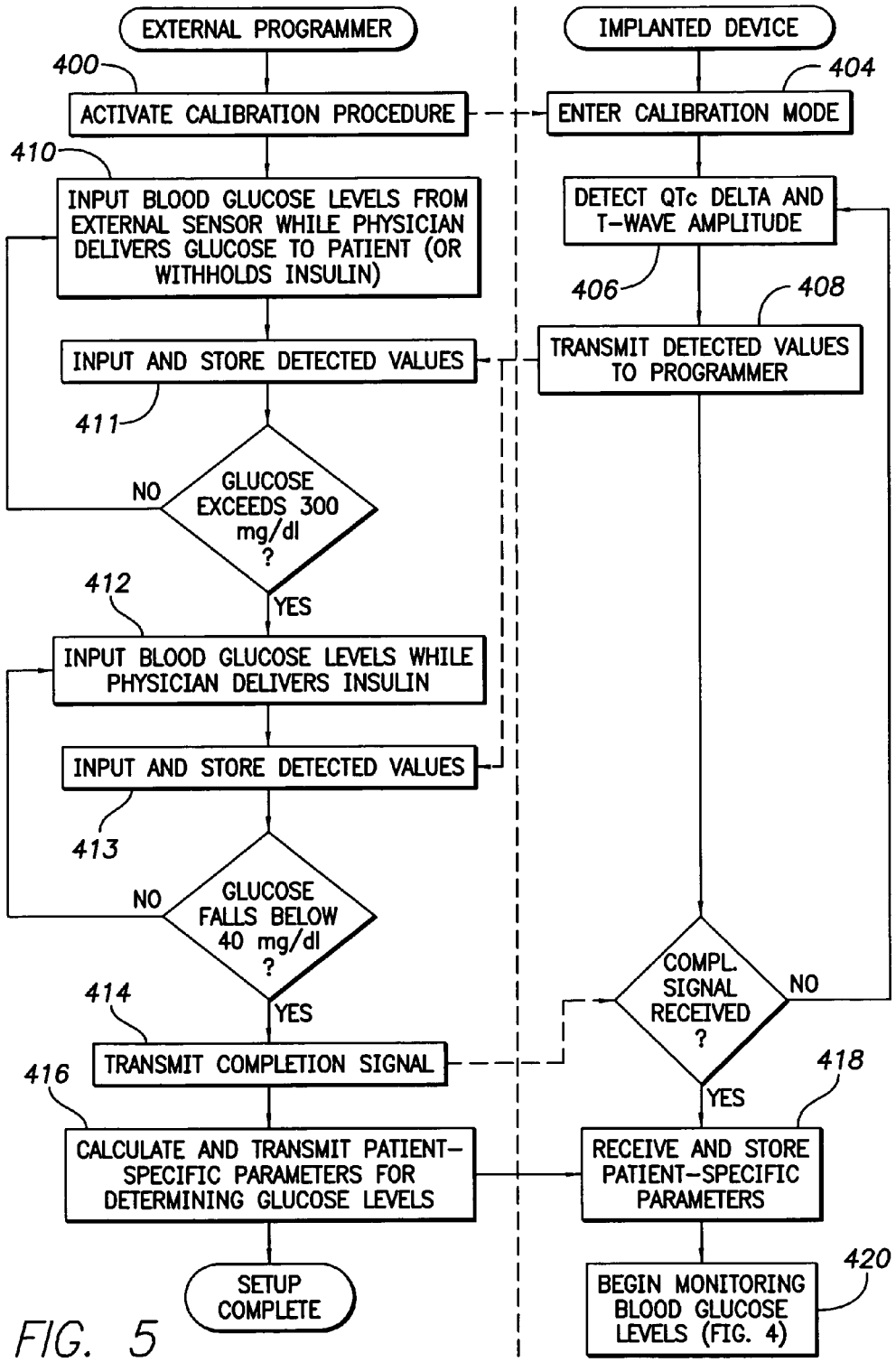
FIG. 5 is a flowchart illustrating a calibration technique performed by both the implanted device of FIG. 2 and the external programmer of FIG. 3 following implantation of the device for determining patient-specific parameters exploited by the technique of FIG. 4.

FIG. 5 is a flowchart illustrating a calibration technique for use following implant of the implantable device for use in determining patient-specific parameters for subsequent use by the glucose monitoring system of FIG. 2 when performing the steps of FIG. 4. FIG. 5 illustrates steps performed by the external programmer of FIG. 3 and by the implanted device of FIG. 2 with steps performed by the external programmer shown on the left and steps performed by the implanted device shown on the right. Initially, at step 400, upon input of appropriate activation commands by a physician operating the external programmer, the calibration system initiates the calibration procedure and transmits a signal to the implanted device for controlling the glucose monitoring system of the implanted device to enter a calibration mode, at step 404. In the calibration mode, the glucose determination unit detects QTc delta values and T-wave amplitude fraction values from electrocardiographic signals, at step 406, but does not derive blood glucose levels. (The determination unit does not derive blood glucose levels because it does not yet have the patient-specific parameters needed to determine the blood glucose levels). Rather, the monitoring system simply transmits the QTc delta values and the T-wave amplitude fraction values to the external programmer, at step 408. Steps 406 and 408 are repeated in a loop until a completion signal is ultimately received.

Meanwhile, the calibration system of the external programmer, at step 410, inputs blood glucose levels derived from an external blood glucose monitor while the physician delivers glucose to the patient either orally or intravenously for the purposes of raising the blood glucose level. Alternatively, if the patient is an insulin-dependent diabetic, the physician merely withholds insulin that would otherwise be provided to thereby allow the blood glucose level to rise. The blood glucose levels input at step 410 may be received automatically from an external blood glucose monitor that is directly coupled to the external programmer or may be input manually by the physician based on information provided by the external blood glucose monitor. Any of a variety of commercially available external blood glucose monitors may be employed. Preferably, however, an external sensor is employed that is capable of substantially continuously monitoring and updating the blood glucose levels such that data can be input substantially continuously at step 410 to provided a precise record of blood glucose levels as a function of QTc delta and T-wave amplitude. Alternatively, though, the blood glucose level may be detected and input periodically, such as once every 10 to 15 minutes. In any case, the blood glucose levels provided by the external blood glucose monitor are recorded in the memory of the external programmer for subsequent use. QTc delta values and T-wave amplitude fraction values detected by the implanted device are received and stored at step 411.

The blood glucose level for the patient is allowed to rise until it exceeds 300 mg/dl, then, beginning at step 412, the physician delivers insulin to the patient to cause the blood glucose level to decrease while the external programmer continues to input the blood glucose levels for the patient derived from the external monitor and continues to receive QTc delta values and T-wave amplitude fraction values detected by the implanted device (which are received and stored at step 413.) The patient blood glucose level is allowed to decrease until it ultimately falls below 40 mg/dl at which point the data collection process is complete and a completion signal is transmitted, at step 414, to the implanted device. Upon receipt of the completion signal, the implanted device suspends detection of QTc delta values and T-wave amplitude fractions.

The patient-specific parameters are then calculated by the external programmer at step 416 and transmitted to the implanted device for storage therein at step 418. Thereafter, at step 420, the implanted device begins monitoring blood glucose levels using the techniques described above with respect to FIG. 4. Although not shown, the external programmer can also input control parameters provided by the physician for transmission to the implanted device, at step 416, for use in controlling the implanted device or the implanted insulin pump based on patient blood glucose levels. For example, the control parameters may specify an optimal blood glucose level so that the implanted device can then control the insulin pump to adjust the amount of insulin delivered to the patient to achieve the optimal blood glucose level. The control parameters may also specify the specific upper and lower bounds used for generating warning signals.

With regard to the calculation of the patient-specific parameters, as a result of steps 410–412, the external programmer records two sets of data: a first set that provides a QTc delta value for each input blood glucose level throughout the range of 40 to 300 mg/dl; and a second set which provides a T-wave amplitude fraction value for each input blood glucose level also throughout the range of 40 to 300 mg /dl. At step 416, the calibration system automatically combines the two sets of data and determines a set of parameters that relate QTc delta values and T-wave amplitude fraction values to patient blood glucose levels. In the example wherein the linear relationship of Eq. 1 is employed, the external programmer calculates the aforementioned T-wave coefficient, QT coefficient, and intercept coefficient for use in Eq. 1 (also referred to herein as coefficients A, B, and C). This may be achieved by using otherwise conventional regression analysis techniques. The linear relationship of Eq. 1 is preferred since it is simple to calculate and appears to provide an adequate equation for deriving the blood glucose levels of the patient. However, other mathematical relationships can instead be employed, including nonlinear equations. In another example, rather than fitting the data to a predetermined mathematical relationship, the system instead generates a lookup table relating QTc delta values and T-wave amplitude fractions to patient blood glucose levels. The lookup table may be generated by interpolating, if needed, between individual data values recorded during steps 410–412. The lookup table is then transmitted to the implanted device so that the device can then simply lookup a value for the blood glucose level for each combination of QTc delta value and T-wave amplitude fraction value. Although the use of a lookup table is certainly feasible, it requires more data to be stored within the implanted device. As can be appreciated a wide range of techniques may be employed for mathematically relating the QTc delta values and T-wave amplitude fraction values to the input blood glucose levels and no attempt is made herein to describe all possible techniques.

EXAMPLE

Figure 6:
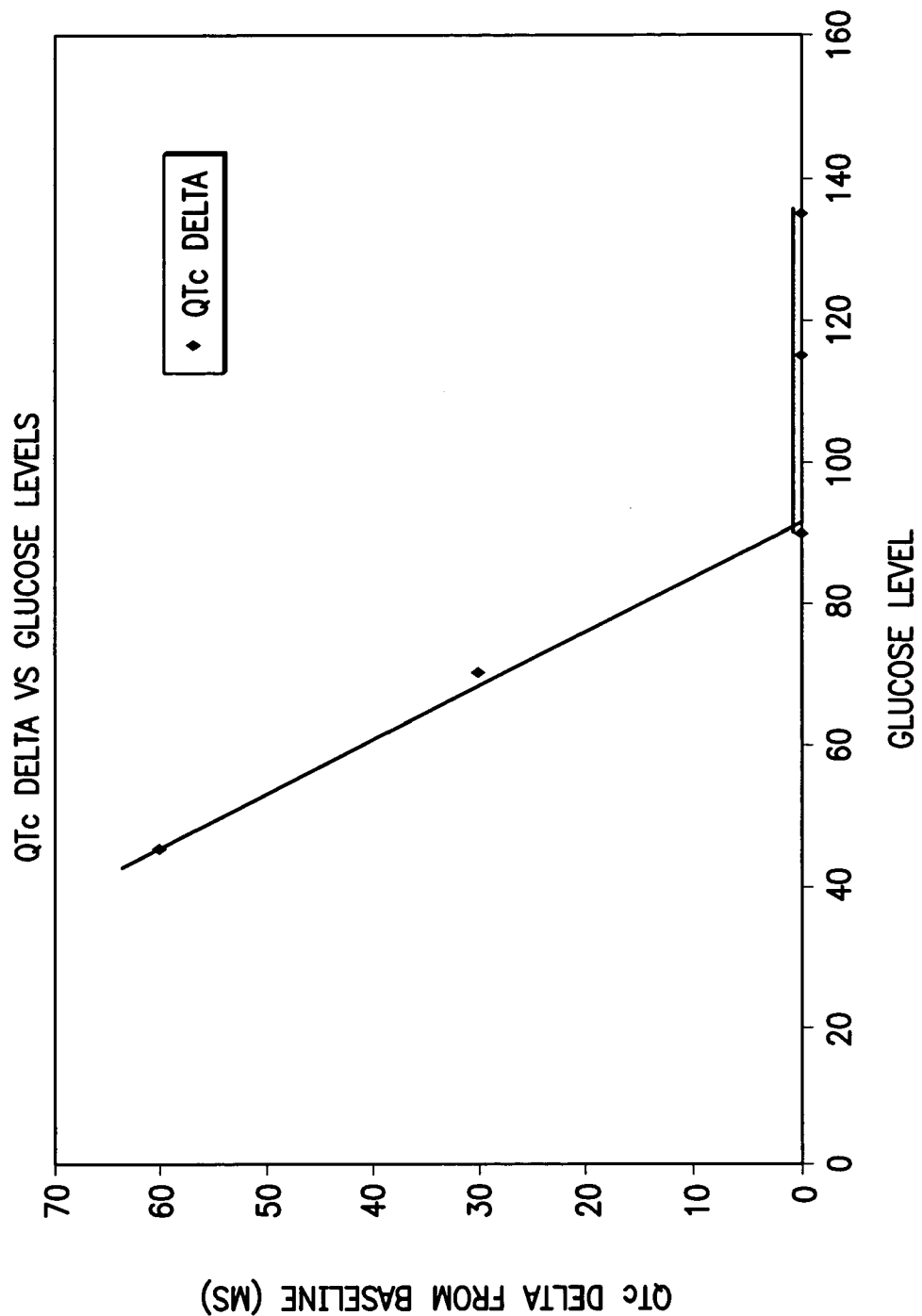
FIG. 6 is a graph illustrating exemplary QTc intervals vs. blood glucose levels.

A specific example of the relation between QTc delta values, T-wave amplitude fractions, and blood glucose levels will now to described with reference to FIGS. 6–8. FIG. 6 illustrates QTc delta values as a function of the blood glucose level for blood glucose levels in the range of 40 mg/dl to about 140 mg/dl. As can be seen, there is a substantially linear relationship between QTc delta and glucose level for glucose levels in the range of 40 mg/dl to about 90 mg/dl. Beyond about 90 mg/dl, QTc delta remains at zero regardless of the blood glucose level. Hence, QTc delta is effective for use as a proxy for blood glucose levels when the blood glucose level is below about 90 mg/dl but is ineffective otherwise. Hence, as explained above, QTc delta is employed in combination with T-wave amplitude fractions for determining blood glucose levels. However, in circumstances wherein blood glucose levels might only need to be determined for levels below about 90 mg/dl, then the QTc delta could be used independently as a proxy for blood glucose levels. As such, of the techniques described herein should not be construed as requiring, in all cases, that QTc delta be used only in conjunction with T-wave amplitude fractions values. Rather, QTc can be used individually as a proxy for blood glucose levels at least within selected ranges of blood glucose levels such as the range below about 90 mg/dl.

Figure 7:
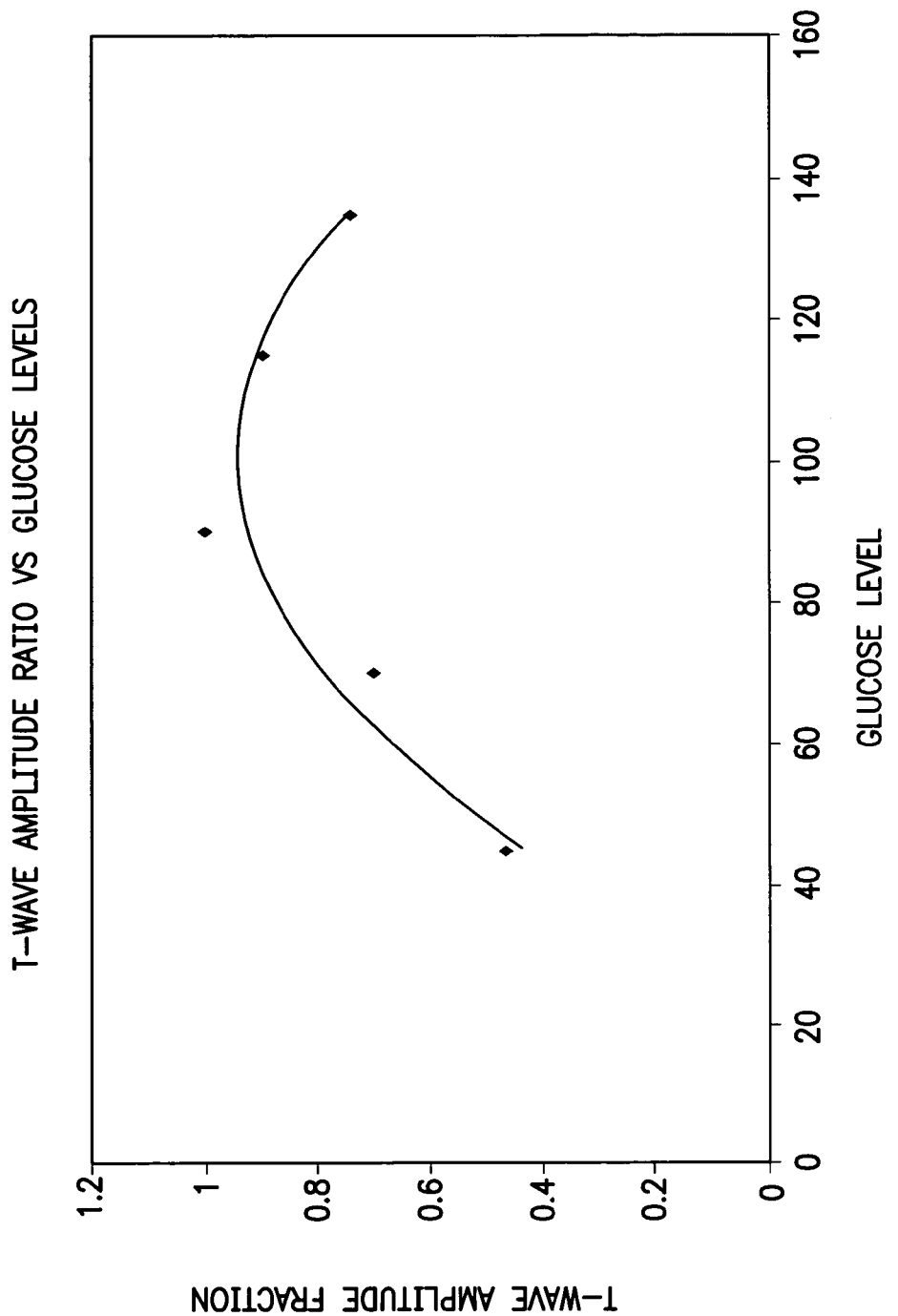
FIG. 7 is a graph illustrating exemplary T-wave amplitude fractions vs. blood glucose levels.

FIG. 7 illustrates the T-wave amplitude fraction as a function of the blood glucose level also for levels in the range of 40 mg/dl to about 140 mg/dl. As can be seen, there is a substantially bimodal relationship between T-wave amplitude fraction and glucose level with T-wave amplitude fraction increasing with rising glucose levels in the range of 40 mg/dl to about 90 mg/dl, then decreasing with rising glucose levels in the range of 90 mg/dl to about 140 mg/dl. In addition, the overall trend of T-wave amplitude as a function of blood glucose level is somewhat nonlinear though it can be approximated by a first linear function below about 90 mg/dl and a second linear function above about 90 mg/dl. Hence, T-wave amplitude fraction appears to be ineffective by itself as a proxy for blood glucose levels since a single T-wave amplitude fraction value, such as 0.8 can correspond to at least two blood glucose level values. Hence, preferably, corrected T-wave amplitude fraction is employed in combination with at least one other cardiac signal feature that demonstrates a substantially monotonically-varying response as a function of blood glucose levels. By monotonically-varying it is meant that the cardiac feature exhibits one and only one value for each value of the blood glucose level, at least within selected ranges of blood glucose values. The primary example provided herein is QTc interval. However, other cardiac signal features may be employed in the alternative such as heart rate variability, QT dispersion (i.e. the difference among QT intervals as measured by different leads), and QT equivalents such as RT or ST intervals.

Figure 8:
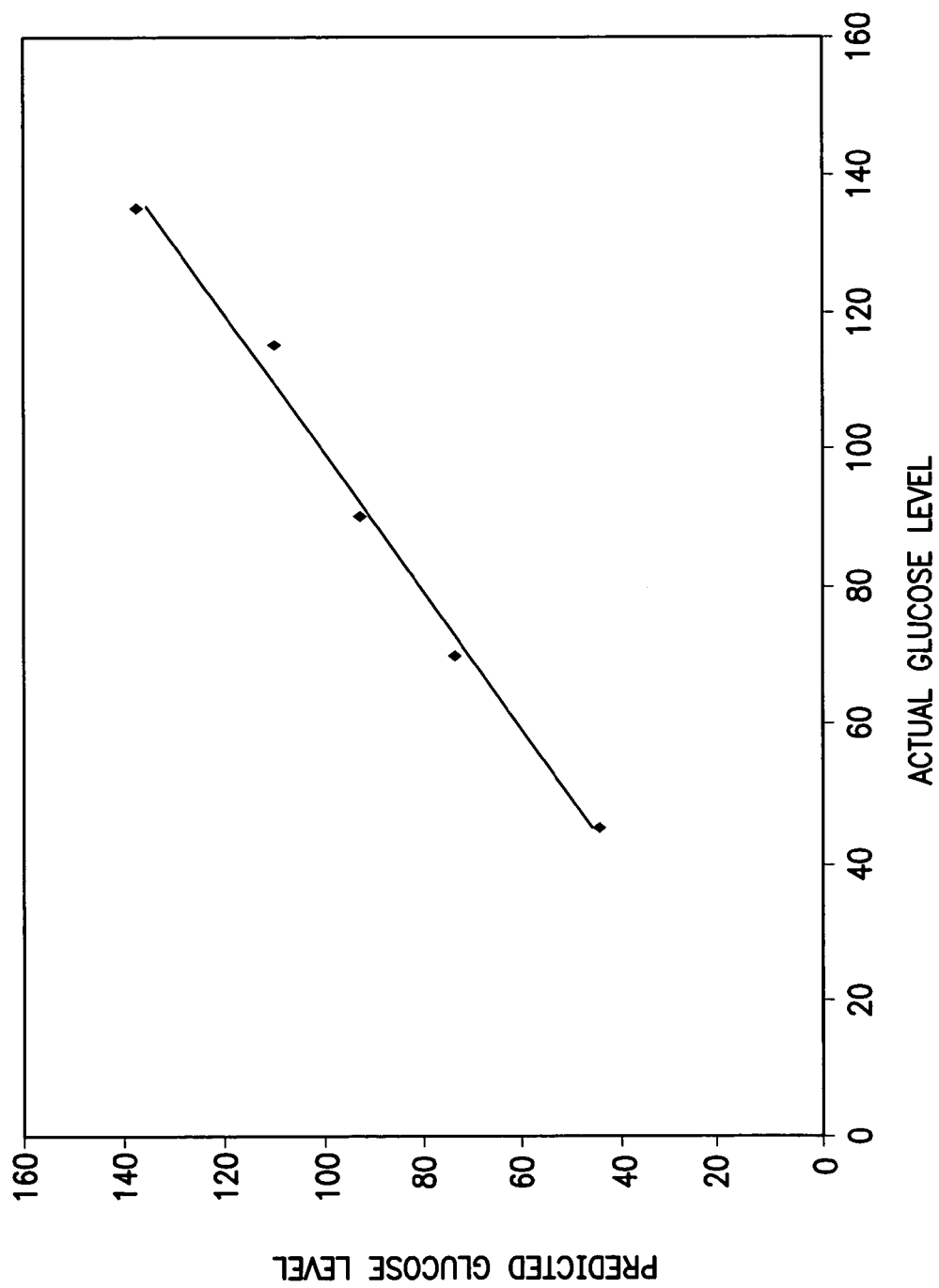
FIG. 8 is a graph illustrating exemplary blood glucose levels vs. actual blood glucose levels as determined using the technique of FIGS. 4–5.

FIG. 8 illustrates predicted blood glucose levels as a function of actual blood glucose levels achieved by fitting the data from FIGS. 6 and 7 to a linear function, specifically the function of Eq. 1. As can be seen, the predicted glucose level closely matches the actual glucose level at each data point and confirms the suitability of using the linear relationship of Eq. 1. The data shown within FIGS. 6–7 is based on information provided within the aforementioned paper by Ireland, et al. The data should not be construed as necessarily representing specific data for any particular actual patient. Some degree variation is to be expected when applying the techniques of the invention to particular patients.

What have been described are various techniques performed by an implantable cardiac stimulation device for monitoring blood glucose levels and performed by an external programmer for calibrating the implantable cardiac stimulation device. However, principles of the invention may be exploiting using other implantable medical devices and other external devices. In addition, while the invention has been described with reference to particular embodiments, modifications can be made thereto without departing from the spirit and scope of the invention.

What is claimed is:

1. A method performed by an external programmer device in communication with an implantable medical device implanted within a patient, the method comprising:
   receiving signals from the implantable device representative of electrical cardiac signals;
   receiving signals representative of corresponding patient blood glucose levels;
   determining parameters relating the electrical cardiac signals to the blood glucose levels for the particular patient; and
   transmitting the parameters to the implantable device such that the implantable device can thereafter derive patient blood glucose levels from subsequently detected electrical cardiac signals.

2. The method of claim 1 wherein receiving signals from the implantable device representative of electrical cardiac signals comprises receiving signals representative of T-wave amplitudes and QT intervals.

3. The method of claim 2 wherein determining parameters relating T-wave amplitudes and QT intervals to blood glucose levels comprises correlating a plurality of blood glucose levels with corresponding T-wave amplitudes and QT intervals based on a pre-determined general functional relationship so as to derive parameters specifying the functional relationship for the particular patient.

4. The method of claim 3 wherein the signals representative of T-wave amplitudes are T-wave amplitude fractions and wherein the signals representative of QT intervals are QTc interval deltas and wherein the pre-determined general functional relationship is:

$$\text{blood glucose level} = A - B*QTc - C*(T\text{-wave amplitude fraction})$$

wherein A, B and C are the parameters to be determined that specify the functional relationship for the particular patient.

5. The method of claim 4 wherein transmitting the parameters to the implantable device comprises:
transmitting the parameters A, B and C to the implantable device.

6. The method of claim 4 wherein correlating a plurality of blood glucose levels with corresponding T-wave amplitude fractions and QTc delta values comprises performing multiple regression statistical analysis on the plurality of blood glucose levels with corresponding T-wave amplitude fractions and QTc delta values.

7. The method of claim 2 wherein receiving signals from the implantable device representative of patient T-wave amplitudes and QT intervals is performed throughout a pre-determined range of blood glucose levels.

8. The method of claim 7 wherein receiving signals from the implantable device further comprises:
receiving signals from the implantable device representative of patient T-wave amplitudes and QT intervals while the blood glucose level of the patient rises to a predetermined upper threshold; and
receiving signals from the implantable device representative of patient T-wave amplitudes and QT intervals while the blood glucose level of the patient decreases from the upper threshold to a pre-determined lower threshold.

9. The method of claim 8 wherein the lower threshold is 40 mg/dl and the upper threshold is 300 mg/dl.

10. The method of claim 1 wherein receiving signals representative of corresponding patient blood glucose levels comprises receiving signals from an external blood glucose monitor.

11. The method of claim 1 wherein the implantable device includes an insulin pump and further comprising generating and transmitting control signals to the implantable device specifying control of the insulin pump based on detected blood glucose levels.

12. The method of claim 1 wherein the implantable device includes the capability of generating warning signals and further comprising generating and transmitting control signals to the implantable device specifying upper and lower blood glucose bounds for use in triggering warning signals.

13. The method of claim 12 wherein the upper bound is 120 mg/dl and the lower bound is 60 mg/dl.

14. An external system for use with an implantable medical device implanted within a patient, the system comprising:
means for receiving signals from the implantable device representative of electrical cardiac signals;
means for inputting signals representative of corresponding patient blood glucose levels;
means for determining parameters relating the electrical cardiac signals to the blood glucose levels for the particular patient; and
means for transmitting the parameters to the implantable device.

15. An external system for use with an implantable medical device implanted within a patient, the system comprising:
a calibration system operative to determine parameters relating electrical cardiac signals of the patient in which the device is implanted to blood glucose levels of the patient; and
a telemetry unit operative to transmit the parameters to the implantable device for use by the implantable device.

16. A method performed by one or more external devices in conjunction with an implantable medical device implanted within a patient, the method comprising:
externally providing for an increase in blood glucose levels within the patient while internally detecting and recording electrical cardiac signals and externally detecting and recording patient blood glucose levels for a plurality of blood glucose levels;
externally decreasing the blood glucose levels while continuing to internally detect and record electrical cardiac signals and externally detect and record patient blood glucose levels for a plurality of blood glucose levels;
externally receiving the recorded electrical cardiac signals and the recorded patient blood glucose levels and determining parameters relating the electrical cardiac signals to the patient blood glucose levels; and
transmitting the parameters to the implanted device for use by the implanted device to derive blood glucose levels for the patient from subsequently detected electrical cardiac signals.

17. The method of claim 16 wherein detecting and recording electrical cardiac signals comprises detecting and recording signals representative of T-wave amplitudes and QT intervals.

18. The method of claim 16 wherein the patient is not an insulin-dependent diabetic and wherein providing for an increase in blood glucose levels within the patient comprises administering glucose to the patient.

19. The method of claim 16 wherein the patient is an insulin-dependent diabetic and wherein providing for an increase in blood glucose levels within the patient comprises withholding insulin from the patient.

* * * * *